US00RE39468E

(19) United States
(12) Reissued Patent
Ricker

(10) Patent Number: US RE39,468 E
(45) Date of Reissued Patent: Jan. 16, 2007

(54) SOIL SAMPLE PROCURING TOOL AND METHOD OF PREPARING SOIL SAMPLE FOR ANALYSIS

(75) Inventor: Michael J. Ricker, DePere, WI (US)

(73) Assignee: Chemisphere, Green Bay, WI (US)

(21) Appl. No.: 10/214,833

(22) Filed: Aug. 8, 2002

(Under 37 CFR 1.47)

Related U.S. Patent Documents

Reissue of:
(64) Patent No.: 6,098,724
Issued: Aug. 8, 2000
Appl. No.: 08/980,904
Filed: Dec. 1, 1997

U.S. Applications:
(63) Continuation of application No. 10/050,800, filed on Jan. 9, 2002, now abandoned.

(51) Int. Cl.
*G01N 1/04* (2006.01)

(52) U.S. Cl. ..... 175/20; 175/58; 73/864.44
(58) Field of Classification Search ..... 175/20, 175/58, 244, 249; 73/864.44, 864.45, 863.21
See application file for complete search history.

(56) References Cited

U.S. PATENT DOCUMENTS

| | | | | | |
|---|---|---|---|---|---|
| 1,109,446 | A | * | 9/1914 | Melberg | 73/864.44 |
| 3,273,930 | A | * | 9/1966 | Gottfried | 73/864.44 |
| 3,326,049 | A | * | 6/1967 | Eley | 73/864.44 |
| 3,444,938 | A | * | 5/1969 | Ballmann | 73/864.44 |
| 3,464,732 | A | * | 9/1969 | Woodward | 294/19.1 |
| 3,596,719 | A | * | 8/1971 | Koziski | 175/20 |
| 4,156,469 | A | * | 5/1979 | Laskey | 175/58 |
| 4,336,849 | A | * | 6/1982 | Hug | 175/246 |
| 4,498,547 | A | * | 2/1985 | Herkness, II | 175/244 |
| 4,549,612 | A | * | 10/1985 | Cushing | 175/20 |
| 4,790,392 | A | * | 12/1988 | Clements | 175/20 |
| 4,809,790 | A | * | 3/1989 | Manchak, Jr. | 175/17 |
| 4,860,599 | A | * | 8/1989 | Griffis | 73/864.45 |
| 4,946,000 | A | * | 8/1990 | Gibson et al. | 175/251 |
| 4,989,678 | A | * | 2/1991 | Thompson | 175/20 |
| 5,038,624 | A | * | 8/1991 | Clay | 73/864.44 |
| 5,050,425 | A | * | 9/1991 | Robbins | 73/19.1 |
| 5,140,845 | A | * | 8/1992 | Robbins | 73/19.03 |
| 5,186,263 | A | * | 2/1993 | Kejr et al. | 175/20 |
| 5,211,249 | A | * | 5/1993 | Richter et al. | 175/20 |
| 5,245,878 | A | * | 9/1993 | Underwood | 73/864.44 |
| 5,307,884 | A | * | 5/1994 | Millgard | 175/20 |

(Continued)

OTHER PUBLICATIONS

"Modified DRO Method for Determining Diesel Range Organics", pp. 1–26, PUBL–SW–141, Wisconsin DNR, Sep. 1995.*
"Modified GRO Method for Determining Gasoline Range Organics", pp. 1–33, PUBL–SW–140, Wisconsin DNR, Sep. 1995.*
Chapter NR 149 (NR 149.03)"Laboratory Certification and Registration", pp. 365–367, Register, Nov. 1996, No. 491.*
NR 700.11 "Sample Preservation and Analysis", Wisconsin Administrative Code NR 700.11, p. 6, Register, Feb. 1997, No. 494.*

*Primary Examiner*—Jennifer H. Gay
(74) *Attorney, Agent, or Firm*—Jansson, Shupe, Munger & Antaramian, Ltd.

(57) ABSTRACT

A tool for withdrawing a soil sample comprising a frame member including a portion including spaced vertically extending legs having lower ends, a foot portion fixed to the lower ends of the legs and including a horizontally extending slot defined by a vertically extending wall including a horizontally extending groove, and an abutment surface extending horizontally and located between the legs in upwardly spaced relation from the foot portion.

38 Claims, 2 Drawing Sheets

U.S. PATENT DOCUMENTS 5,322,133 A * 6/1994 Hart ..... 175/20
5,343,771 A * 9/1994 Turriff et al. ..... 73/864.44
5,344,781 A * 9/1994 Kitchen et al. ..... 436/29
5,384,262 A * 1/1995 Piasio et al. ..... 436/518
5,450,913 A * 9/1995 Mefferd et al. ..... 175/58
5,474,141 A * 12/1995 Hart ..... 175/20
5,505,098 A * 4/1996 Turriff et al. ..... 73/864.44
5,517,868 A * 5/1996 Turriff et al. ..... 73/864.44
5,522,271 A * 6/1996 Turriff et al. ..... 73/864.44
5,587,538 A * 12/1996 Bratton ..... 73/863.33
5,606,139 A * 2/1997 Wittig et al. ..... 73/864.44
5,624,554 A * 4/1997 Faulkner et al. ..... 210/232
5,658,463 A * 8/1997 Rubio ..... 210/634
5,706,904 A * 1/1998 Turriff et al. ..... 175/20
5,777,242 A * 7/1998 Zuidberg et al. ..... 73/864.45
6,357,535 B1 * 3/2002 Lemon ..... 175/20

* cited by examiner

SOIL SAMPLE PROCURING TOOL AND METHOD OF PREPARING SOIL SAMPLE FOR ANALYSIS

Matter enclosed in heavy brackets [ ] appears in the original patent but forms no part of this reissue specification; matter printed in italics indicates the additions made by reissue.

*RELATED APPLICATION AND CLAIM OF PRIORITY*

*This application is a continuation of Reissue application Ser. No. 10/050,800 having a filing date of Jan. 9, 2002, now abandoned, which is a reissue of Ser. No. 08/980,904 having a filing date of Dec. 1, 1997, now U.S. Pat. No. 6,098,724.*

BACKGROUND OF THE INVENTION

The invention relates generally to soil sampling, to tools for extracting a soil sample from the ground, and to methods of procuring and handling a soil sample until subsequent analysis.

The invention also relates to methods and apparatus for procuring and handling soil samples containing volatile components, such as gasoline or other ground contaminants.

Attention is directed to the following U.S. Patents:

U.S. Pat. No. 4,498,547, Herkness, II, issued Feb. 12, 1985

U.S. Pat. No. 4,790,392, Clements, issued Dec. 13, 1988

U.S. Pat. No. 4,809,790, Manchak, Jr., issued Mar. 7, 1989

U.S. Pat. No. 4,946,000, Gibson et al., issued Aug. 7, 1990

U.S. Pat. No. 4,989,678, Thompson, issued Feb. 5, 1991

U.S. Pat. No. 5,038,624, Clay, issued Aug. 13, 1991

U.S. Pat. No. 5,050,425, Robbins, issued Sep. 25, 1991

U.S. Pat. No. 5,140,845, Robbins, issued Aug. 25, 1992

U.S. Pat. No. 5,186,263, Kejr et al., issued Feb. 16, 1993

U.S. Pat. No. 5,343,771, Turriff et al., issued Sep. 6, 1994

U.S. Pat. No. 5,344,781, Kitchen et al., issued Sep. 6, 1994

U.S. Pat. No. 5,384,262, Piasio et al., issued Jan. 24, 1995

U.S. Pat. No. 5,450,913, Mefferd et al., issued Sep. 19, 1995

U.S. Pat. No. 5,505,098, Turriff et al, issued Apr. 9, 1996

U.S. Pat. No. 5,517,868, Turriff et al., issued May 21, 1996

U.S. Pat. No. 5,522,271, Turriff et al., issued Jun. 4, 1996

U.S. Pat. No. 5,587,538, Bratton, issued Dec. 24, 1996

U.S. Pat. No. 5,606,139, Wittig et al., issued Feb. 25, 1997

Attention is also directed to the following publications:

"Modified DRO Method for Determining Diesel Range Organics", pp. 1–26; PUBL-SW-141; Wisconsin DNR, September 1995

"Modified GRO Method for Determining Gasoline Range Organics", pp. 1–33; PUBL-SW-140; Wisconsin DNR, September 1995

Chapter NR 149 (NR 149.03) "Laboratory Certification and Registration", pp. 365–367, Register, November, 1996, No. 491

NR 700.11 "Sample Preservation and Analysis", Wisconsin Administrative Code NR 700.11, page 6, Register, February, 1997, No. 494

SUMMARY OF THE INVENTION

The invention provides a method for taking a soil sample, which method comprises the steps of providing a hollow member having an open end, forcing the open end of the hollow member into the ground to locate a soil sample in the hollow member, ejecting the soil sample from the hollow member and into a sealable vial, sealing the vial, thereafter injecting methanol or other suitable organic material capturing agent into the vial without opening the vial, and thereafter analyzing the contents of the vial.

The invention also provides a method of taking a soil sample, which method comprises the steps of providing a hollow member having an open end, a plunger housed in the hollow member, and a sealable vial having a self-sealing penetrable part, forcing the open end of the hollow member into the ground to locate a soil sample in the hollow member, promptly ejecting the soil sample from the hollow member by the plunger and into the sealable vial, promptly sealing the vial, thereafter injecting through the penetrable part a first quantity of methanol into the vial, shake for fifteen seconds and thereafter adding to the vial a second quantity of methanol, if necessary, such that the total volume of methanol in milliliters in the vial is equal to the weight in grams of the soil sample in the vial, and analyzing the contents of the vial.

The invention also provides a tool for withdrawing a soil sample, the tool including a frame member having spaced upright legs and a foot portion fixed to the lower ends of the legs. The foot portion includes a slot adopted to removably house a horizontal flange projecting from the upper end of an elongated hollow cylindrical member. The elongated cylindrical member is open at its lower end and is adapted to be forced into the ground. In one form of the invention, the elongated cylindrical member can be a syringe having the end removed. The tool also includes a plunger member housed in the elongated hollow cylindrical member and having an upper projecting end located between the legs of the frame member. The plunger is supported for slideable movement within the hollow member and includes an upper end engageable with the abutment portion of the frame member to restrict the extent of upward movement of the plunger member during insertion of the tubular member into the ground. The apparatus of the invention also includes a vial for receiving a soil sample from the elongated cylindrical member, the vial including a removable cap having a septum. The septum is intended to permit injection of methanol or other organic capturing agent into the vial without opening the vial.

Other features and advantages of the invention will become apparent to those skilled in the art upon review of the following detailed description, claims and drawings.

Figure 1:
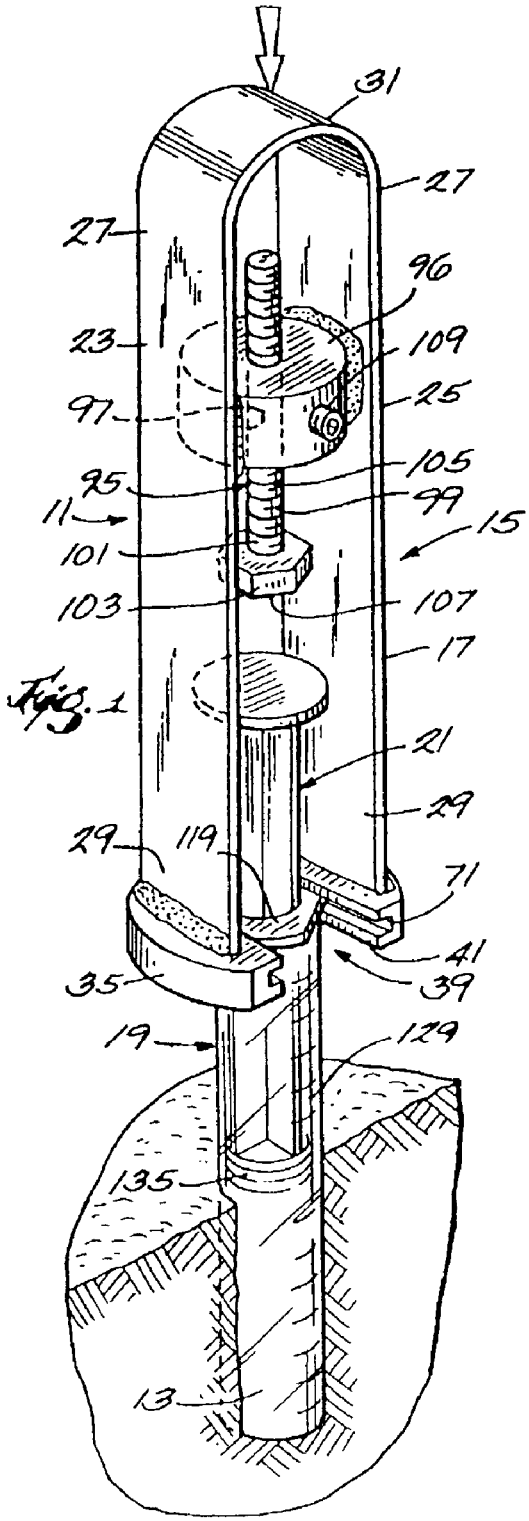
FIG. 1 is a perspective view of a tool for withdrawing a soil sample, which tool incorporates various of the features of the invention.

Before one embodiment of the invention is explained in detail, it is to be understood that the invention is not limited in its application to the details of the construction and the arrangements of components set forth in the following description or illustrated in the drawings. The invention is capable of other embodiments and of being practiced or being carried out in various ways. Also, it is understood that the phraseology and terminology used herein is for the purpose of description and should not be regarded as limiting.

DESCRIPTION OF THE PREFERRED EMBODIMENT

Shown in FIG. 1 of the drawings is a tool 11 for withdrawing a soil sample 13, which tool 11 comprises a frame member 15 including an inverted U-shaped handle or guard portion 17, an elongated hollow member 19 adapted to be inserted into the ground and extending downwardly from the frame member 17 and, a plunger member 21 located, in part, within the frame member 15 and, in part, for slideable movement within the hollow member 19.

More particularly, the frame member 15 can be fabricated of any suitable strong and rigid material, such as plastic or metal, and includes horizontally spaced upright legs 23 and 25 having upper and lower ends 27 and 29, and a bridge 31 connecting the upper ends 27 of the legs 23 and 25.

Figure 4:
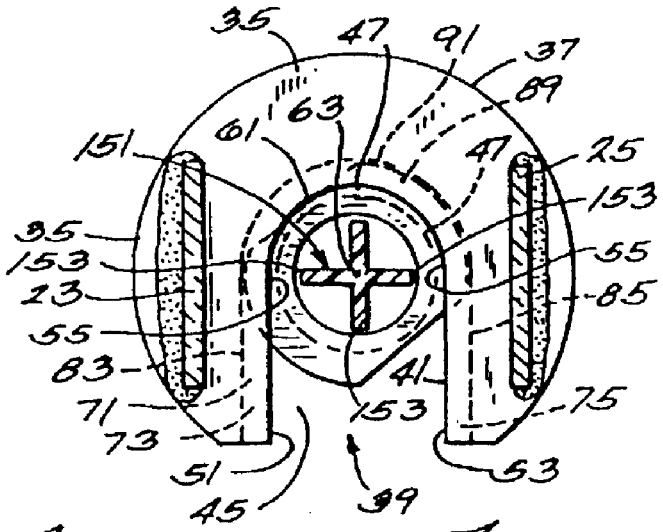
FIG. 4 is a sectional view taken along line 4—4 of FIG. 3.
Figure 3:
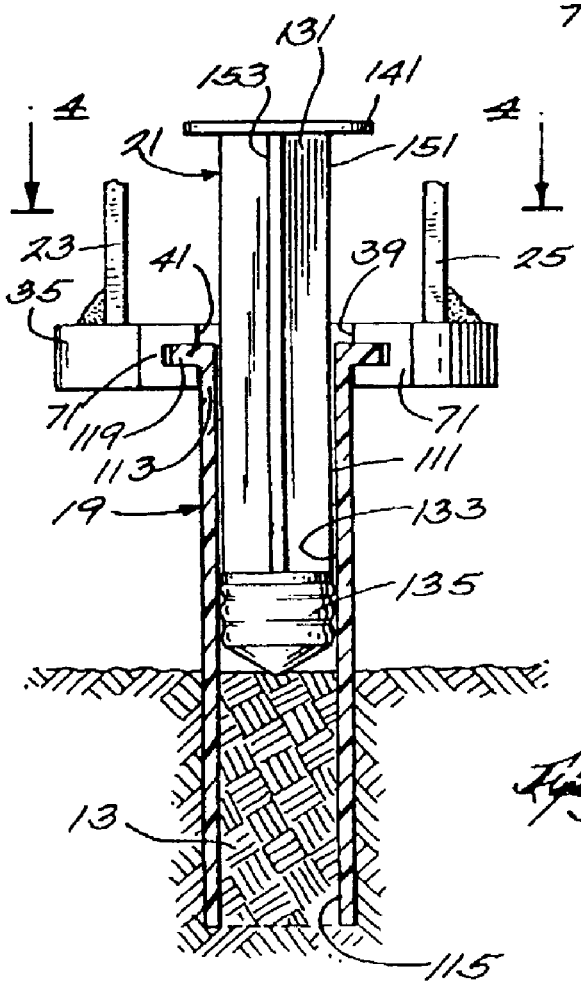
FIG. 3 is a side elevational view, partially in section, of a portion of the tool shown in FIG. 1.

In addition, the frame member 15 includes a foot portion 35 fixed to the lower ends 29 of the legs 23 and 25 and including, as best shown in FIG. 4, an outer perimeter 37 extending laterally beyond the spaced legs 23 and 25 and a slot 39 defined by a vertically extending wall 41. The slot 41 includes an entry part 45, and a semi-circular part 47 which extends from the entry part 45 and is located between the legs 23 and 25. More particularly, while other constructions can be employed, in the disclosed construction, the vertically extending wall 41 includes a pair of horizontally spaced straight and parallel portions 51 and 53 which define the entry part 45 and which include inner ends 55, and a semi-circular portion 61 which defines the semi-circular part 47 and which extends about an axis 63 and from the inner ends 55 of the straight portions 51 and 53 of the vertically extending wall 41.

The slot 39 also includes a groove 71 which is located in the vertically extending wall 41 and which extends horizontally. More particularly, while other constructions can be employed, in the disclosed construction, the groove 71 includes a pair of horizontally spaced straight and parallel portions 73 and 75 which are respectively located in the straight portions 51 and 53 of the vertically extending wall 41 and which respectively include inner ends. Still more particularly, the straight portions 73 and 75 of the groove 71 respectively include inner vertically extending straight wall surfaces 83 and 85 spaced horizontally from the straight portions 51' and 53 of the vertically extending wall 41 at a first distance.

In addition, the groove 71 includes a circular portion 89 located in the semi-circular portion 61 of the vertically extending inner wall 41 and extending from the inner ends of the straight portions 73 and 75 of the groove 71. More particularly, the circular portion 89 of the groove 71 has an inner vertically extending cylindrical wall surface 91 extending at a common radius from the axis 63 of the semi-cylindrical portion 61 of the slot 39 and spaced horizontally form the semi-cylindrical portion 61 of the vertically extending wall 41 at a second distance greater than the first distance, i.e., greater than the spacing of the straight wall surfaces 83 and 85 from the straight wall portions 51 and 53 of the wall 41.

Still further in addition, the frame member 15 includes (see FIG. 1) an abutment portion 95 which includes a horizontally extending cross member 96 which is fixed to and extends from and between the legs 23 and 25 in upwardly spaced relation from the foot portion 35 and which includes therein a vertically extending threaded bore 97.

Threadedly and adjustably received in the threaded bore 97 is an abutment member 99 which can take any suitable form and which, in the disclosed construction, is in the form of a bolt 101 including a head 103 located below the horizontal cross member 96, and a threaded stem 105 which extends upwardly from the head 103 and is threadedly engaged in the threaded bore 97 in the horizontal cross member 96. The head 103 of the bolt 101 includes a lower surface 107 constituting an abutment surface which will be referred to hereinafter. Accordingly, the location of the abutment surface 107 can be varied relative to the frame member 15. The abutment portion 95 can also include a set screw 109 to prevent inadvertent displacement of the bolt 101 in the cross member 96.

Figure 2:
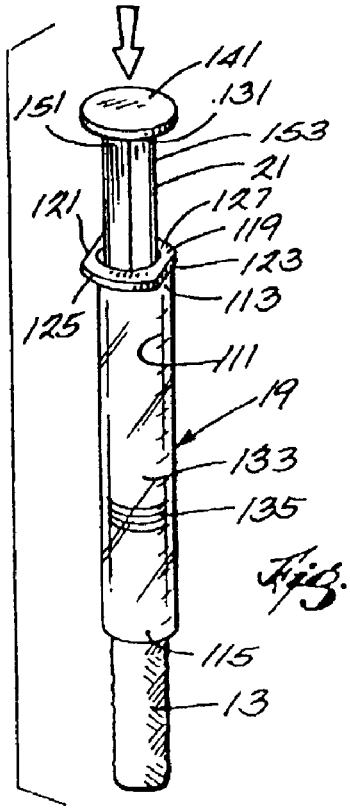
FIG. 2 is a perspective view of the assembly of a hollow member and a plunger member included in the tool shown in FIG. 1.

The elongated hollow member 19 can be fabricated of any suitable material and, in the disclosed construction, is fabricated of clear plastic material and is preferably sturdy and thin walled. While other constructions can be employed, in the disclosed construction, the elongated hollow member 19 is cylindrically shaped and includes an axis which, when the hollow member 19 is assembled with the frame member 15, is coincident with the axis 63. Still more particularly, the elongated hollow member 19 includes (see FIG. 2) an inner cylindrical wall or surface 111, open upper and lower ends 113 and 115, and a flange 119 extending horizontally outwardly from the upper end 113 and removably located in the groove 71 formed in the slot 39 of the foot portion 35 of the frame member 15.

More particularly, while other constructions can be employed, in the disclosed construction, the flange 119 includes a pair of horizontally spaced straight and parallel edges 121 and 123 which are horizontally spaced at a distance slightly less than the horizontal spacing between the straight wall surfaces 83 and 85 of the groove 71. In addition, the flange 119 includes a pair of opposed circular edges 125 and 127 which extend from and between the straight edges 121 and 123 in concentric relation to the axis of the hollow cylindrical member 19 and which are spaced horizontally from the axis of the cylindrical member 19 at a distance slightly less than the horizontal spacing of cylindrical wall surface 91 of the groove 71 from the axis 63 of the semi-cylindrical part 47 of the slot 39 in the foot 35 of the frame member 15.

If desired, a legend 129 indicating the volume of the soil sample 13 can be provided axially on the elongated hollow member 19.

The plunger member 21 can be fabricated of any suitable material and, in the disclosed construction, is fabricated of clear plastic material and includes upper and lower ends 131 and 133, and, at the lower end 133 thereof, a piston 135 which resiliently and sealingly engages the inner wall 111 of the elongated hollow member 19. In addition, the plunger member 21 includes, at the upper end 131 thereof, a horizontally extending portion or cap 141 which is engageable with the abutment surface 107 on the bolt 101 which is adjustably carried by the frame member 15, thereby to prevent unwanted upward movement of the plunger member 21 during insertion of the elongated hollow member 19 into the ground or soil.

Still more particularly, while other constructions can be employed, in the disclosed construction, the plunger member 21 includes a stem 151 which extends downwardly from the upper end 131 thereof, and which has a cross shaped horizontal cross-section and vertically extending edges 153 engaging the inner wall 111 of the elongated hollow member 19 so as to guide movement of the plunger member 21 relative to the elongated hollow member 19.

In a further preferred form of the invention, the elongated hollow member can comprise a suitable plastic medical syringe with the lower end cut off. The elongated hollow member can thus comprise a very inexpensive disposable component.

In use, the assembly of the elongated hollow member 19, with the plunger member 21 partially inserted therein, is located in the tool 11 by sliding the flange 119 of the elongated hollow member 19 into the groove 71 formed in the slot 39 in the foot portion 35 of the frame member 15 and so that the cap or horizontally extending portion 141 of the plunger member 21 is located below the abutment surface 107 of the frame member 15. As thus assembled, the plunger member 21 is generally located between the legs 23 and 25 of the frame member 15 and the hollow elongated member 19 extends outwardly of and downwardly from the foot portion 35 of the frame member 15. When thus assembled, the elongated hollow member 19 is fixed against axial movement relative to the frame member 15 by reason of the engagement of the flange 119 in the groove 71, and the cap 141 of the plunger member 21 is located for movement upwardly until engagement with the abutment surface 107 of the frame member 15, thereby limiting upward movement of the plunger member 21 relative to the elongated hollow member 19.

The elongated hollow member 19 supported by the tool 11 can be forcibly inserted into the soil or ground, with the soil or ground entering into the hollow interior of the tubular member 19 and engaging the piston 135 and the plunger member 21 to displace them upwardly into engagement with the abutment surface 107, thereby limiting further entry of soil into the hollow member 19 to define the soil sample 13 of fixed predetermined volume.

Figure 5:
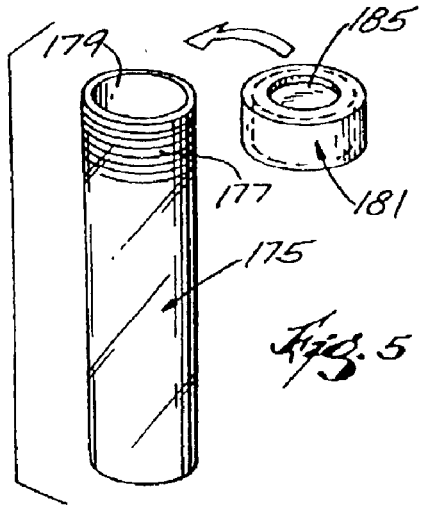
FIG. 5 is a perspective view of a vial or container employed in a method in accordance with the invention.

Thereafter, the assembly of the elongated hollow member 19 and the plunger member 21 is immediately removed from the frame member 15 and the plunger member 21 is immediately manipulated to inwardly displace the plunger member 21 relative to the elongated hollow member 19, thereby displacing the soil sample 13 from the elongated hollow member 19. The soil sample 13 is immediately discharged from the hollow member 19 into a vial or container 175, which is shown in FIG. 5. The container 175 has a larger interior volume than the volume of the soil sample 13, and is sealable so as to prevent loss of any volatile component of the soil sample 13 and to also prevent interaction between the soil sample 13 in interior of the container or vial 175 and the exterior atmosphere. In addition, the vial or container 175 includes a self-sealing penetrable portion or part which will be referred to hereinafter.

While other constructions can be employed, in the disclosed construction, the container or vial 175 is fabricated of plastic and includes a container portion 177 including an open, exteriorly threaded mouth 179. In addition, the vial or container 175 includes an interiorly threaded cap portion 181 which can be tightly threaded on the mouth 179 of the container portion 177 to seal the contents of the container or vial 175. Preferably, the cap portion 181 is provided, in the top surface thereof, with a self-sealing diaphragm or septum 185 which can be penetrated by an injection needle.

After the soil sample is deposited in the container portion 177, the cap portion 181 is immediately threaded on the container portion 177 to seal the container or vial 175.

Thereafter, the sealed container or vial 175 is transported to a laboratory for analysis of the soil sample 13. The diaphragm 185 is pierced by a hypodermic needle, twenty-two gauge or less, (not shown) and a quantity of methanol or other capturing agent is injected into the vial or container 175, which quantity preferably is sufficient to capture any volatile component in the soil sample 13. The vial can then be opened to add to the container or vial 175 a further volume of methanol so that the total volume is milliliters of methanol is approximately equal to the weight in grams of the soil sample 13. The vial can then be stored until analysis of the soil sample.

Thus, the above described tool 11 is employable in a method of taking a soil sample, which method comprises the steps of providing a hollow member having an open end, forcing the open end of the hollow member into the ground to locate a soil sample in the hollow member, displacing or ejecting the soil sample from the hollow member and directly into a sealable container or vial, promptly sealing the container or vial, thereafter injecting methanol or capturing agent into the vial without otherwise compromising or disturbing the sealed condition of the vial or container and thereafter analyzing the contents of the vial.

In a preferred embodiment, the method further includes injecting a sufficient quantity of methanol into the vial that the volume of methanol in milliliters in the vial is approximately equal to the weight in grams of the soil sample in the vial.

Various of the features are set forth in the following claims.

I claim:

1. A method of taking a soil sample, said method comprising the steps of providing a hollow member having an open end, a plunger housed in the hollow member, and a sealable vial having a self-sealing penetrable part, forcing the open end of the hollow member into the ground to locate a soil sample in the hollow member, ejecting the soil sample from the hollow member by the plunger and into the sealable vial, sealing the vial, thereafter injecting through the penetrable part a first quantity of capturing agent into the vial, shake for fifteen seconds, thereafter introducing a second quantity of capturing agent into the vial, and analyzing the contents of the vial.

2. A method of taking a soil sample in accordance with claim 1 and further including providing the hollow member with a second end spaced form the open end, and an outwardly extending flange at the second end thereof, providing a tool having a slot including a groove, and inserting the second end of the hollow member into the slot so as to locate the flange of the hollow member in the groove.

3. A tool for withdrawing a soil sample, said tool comprising a frame member including a portion including spaced vertically extending legs having lower ends, a foot portion fixed to said lower ends of said legs and including a horizontally extending slot defined by a vertically extending wall including a horizontally extending groove, and an abutment surface extending horizontally and located between said legs in upwardly spaced relation from said foot portion.

4. A tool for withdrawing a soil sample, said tool comprising a frame member including an inverted U-shaped guard portion including spaced upright legs having lower ends, a foot portion fixed to said lower ends of said legs, and including an outer perimeter extending laterally beyond said spaced leg portions, a slot defined by a vertically extending wall and including an entry part, and a semi-circular part extending from said entry part and located between said legs, and a groove located in said wall, extending horizontally, and adapted to removably receive a flange at the top end of a hollow member which, when said flange is received in said groove, extends downwardly from said foot portion, which also includes an open lower end, and which has slideable located therein a plunger member extending, in part, above said hollow member and between said spaced legs and having an upper end, and an abutment portion extending horizontally and located between said legs in upwardly spaced relation from said foot portion, and adapted to engage the upper end of the plunger member to maintain the plunger member in a predetermined position relative to the hollow member when the flange is received in said annular groove.

5. A tool for withdrawing a soil sample, said tool comprising a frame member including an inverted U-shaped guard portion including spaced upright legs having lower ends, a foot portion fixed to said lower ends of said legs and including an outer perimeter extending laterally beyond said spaced legs, a slot defined by a vertically extending wall and including an entry part, a semi-circular part extending from said entry part and located between said legs, and a groove located in said wall and extending horizontally, and an abutment portion extending horizontally between said legs in upwardly spaced relation from said foot portion, an elongated hollow cylindrical member adapted to be inserted into the ground, extending downwardly from said foot portion, and including an inner wall, upper and lower ends, and a flange extending horizontally outwardly from said upper end and removably located in said groove, and a plunger member located, in part, between said legs and, in part, for slideable movement within said elongated hollow cylindrical member and including upper and lower ends, and a piston seal engaging said inner wall of said elongated hollow cylindrical member, and a horizontally extending portion at said upper end thereof engageable with said abutment portion of said frame member to prevent upward movement of said plunger member during insertion of said elongated hollow cylindrical member into the ground.

6. A tool in accordance with claim 5 wherein said plunger member includes a stem extending downwardly from said upper end thereof and having a cross shaped horizontal cross-section, and vertically extending edges engaging said inner wall of said hollow member, and a cap located at said upper end, fixed to said stem and including said horizontally extending portion.

7. A tool in accordance with claim 5 wherein said piston resiliently engages said inner wall of said elongated hollow cylindrical member.

8. A tool in accordance with claim 5 wherein said frame member includes a horizontal portion extending from and between said legs, and wherein said abutment portion includes an abutment member which is adjustably fixed in said horizontal portion.

9. A tool in accordance with claim 8 wherein said horizontal portion includes a vertically extending threaded bore, and wherein said abutment member comprises a bolt including a head located below said horizontal portion, and a threaded stem extending upwardly from said head and threadedly engaged in said threaded bore in said horizontal portion.

10. A tool in accordance with claim 5 wherein said cylindrical member includes an axis, and wherein said flange includes a pair of horizontally spaced straight edges, and a pair of opposed circular edges extending from and between said straight edges in concentric relation to said axis of said cylindrical member.

11. A tool in accordance with claim 5 wherein said vertically extending wall includes a pair of horizontally spaced straight portions defining said entry part and including inner ends, and a semi-circular portion defining said semi-circular part and extending from said inner ends of said straight portions of said vertically extending wall, and wherein said groove includes a pair of horizontally spaced straight portions located in said straight portions of said vertically extending wall and including inner ends, and a circular portion located in said semi-circular portion of said inner wall and extending from said inner ends of said straight portions of said groove.

12. A tool in accordance with claim 11 wherein said cylindrical member includes an axis, wherein said straight portions of said groove respectively have inner vertically extending straight wall surfaces spaced horizontally from said straight portions of said vertically extending wall at a first distance, wherein said circular portion of said groove has an inner vertically extending circular wall surface extending at a constant radius from said axis of said cylindrical member, concentrically with said axis of said cylindrical member, and spaced horizontally from said semi-cylindrical portion of said vertically extending wall at a second distance greater than said first distance, and wherein said flange includes a pair of horizontally spaced straight edges which are horizontally spaced at a distance slightly less than the horizontal spacing between said straight wall surfaces of said groove, and a pair of opposed circular edges which extend concentrically with said axis of said cylindrical member, and which are spaced horizontally from said axis of said cylindrical member at a distance slightly less than the spacing of said circular wall surface from said axis of said cylindrical member.

*13. A soil sampling device comprising:*

*a housing defining an open inner chamber, the housing having a first end and a second end;*

*an opening formed in the second end of the housing and defining a passageway from outside the housing to the inner chamber;*

*a groove at least partially surrounding the passageway;*

*a tube formed to include a flange, the flange engageable with the groove to couple the tube to the housing; and*

*a plunger slidably positioned within the tube and moveable over a distance between a first position wherein a tail of the plunger is toward the flange of the tube and a second position wherein the tail of the plunger is away from the flange and abuts an abutment surface within the inner chamber of the housing.*

*14. The soil sampling device of claim 13 wherein the distance can be varied.*

*15. A soil sampling device comprising:*

*a housing having a first and second end and defining an open inner chamber and a longitudinal axis, the second end of the housing including an opening providing a passageway from outside the housing to the inner chamber;*

*a groove formed in the opening;*

*an abutment surface positioned within the inner chamber and moveable along the longitudinal axis;*

*a tube formed to include a flange engageable with the groove to couple the tube to the housing; and*

*a plunger slidably positioned within the tube and having an end moveable between a first position toward the*

*flange and a second position away from the flange and abutting the abutment surface.*

*16. A soil sampling device comprising:*

*a hollow housing including a moveable abutment surface positioned within the housing;*

*a tube coupled to the housing; and*

*a plunger having an end, the plunger slidably positioned within the tube and moveable between a first position wherein the plunger end abuts the tube and a second position wherein the plunger end abuts the abutment surface.*

*17. The soil sampling device of claim 16 wherein the tube further includes a flange positioned within a groove in the housing.*

*18. The soil sampling device of claim 16 wherein the first position is spaced apart from the second position by an adjustable distance.*

*19. A method of taking a soil sample for volatile-component analysis, the method comprising the steps of:*

*providing a hollow member having an open end,*

*forcing the open end of the hollow member into the ground to locate a soil sample in the hollow member,*

*ejecting the soil sample from the hollow member and into a sealable vial,*

*sealing the vial with a cap, the sealed vial having a self-sealing penetrable part,*

*thereafter injecting a capturing agent through the self-sealing penetrable part into the vial without otherwise disturbing the sealed condition of the vial, and*

*thereafter analyzing the contents of the vial.*

*20. The method of claim 19 wherein the capturing agent is methanol.*

*21. The method of claim 19 further including storing the sealed vial containing the soil sample and the capturing agent before the analyzing step.*

*22. The method of claim 19 wherein the hollow member is an elongated cylindrical member having a plunger housed therein and the ejecting step comprises sliding the plunger within the hollow member.*

*23. The method of claim 22 further comprising:*

*providing the hollow member with a second end which is spaced from the open end and has an outwardly extending flange,*

*providing a frame member with a foot portion having a flange-receiving groove, and*

*engaging the hollow member with the frame member by inserting the flange into the flange-receiving groove in preparation for the forcing step.*

*24. The method of claim 23 wherein the plunger has a top end and the frame member supports an adjustable abutment member thereon in position above the plunger top end when the hollow member and the frame member are engaged and the method further includes setting a fixed predetermined soil sample volume by adjusting the position of the abutment member.*

*25. The method of claim 24 further including storing the sealed vial containing the soil sample and the capturing agent before the analyzing step.*

*26. A method of taking a soil sample from a sample site for volatile-component analysis at a sample processing site, the method comprising the steps of:*

*providing a hollow member having an open end,*

*forcing the open end of the hollow member into the ground to locate a soil sample in the hollow member,*

*ejecting the soil sample from the hollow member into a sealable vial,*

*sealing the vial with a cap, the sealed vial having a self-sealing penetrable part,*

*before sampling analysis, transporting the sealed vial from the sample site to the processing site,*

*injecting a capturing agent into the vial at the processing site through the self-sealing penetrable part without otherwise disturbing the sealed condition of the vial, and*

*thereafter analyzing the contents of the vial.*

*27. The method of claim 26 wherein the capturing agent is methanol.*

*28. The method of claim 26 further including storing the sealed vial containing the soil sample and the capturing agent before the analyzing step.*

*29. The method of claim 26 wherein the hollow member is an elongated cylindrical member having a plunger housed therein and the ejecting step comprises sliding the plunger within the hollow member.*

*30. The method of claim 29 further comprising:*

*providing the hollow member with a second end which is spaced from the open end and has an outwardly extending flange,*

*providing a frame member with a foot portion having a flange-receiving groove, and*

*engaging the hollow member with the frame member by inserting the flange into the flange-receiving groove in preparation for the forcing step.*

*31. The method of claim 30 wherein the plunger has a top end and the frame member supports an adjustable abutment member thereon in position above the plunger top end when the hollow member and the frame member are engaged and the method further includes setting a fixed predetermined soil sample volume by adjusting the position of the abutment member.*

*32. The method of claim 31 further including storing the sealed vial containing the soil sample and the capturing agent before the analyzing step.*

*33. A method of taking a soil sample for volatile-component analysis, the method comprising the steps of:*

*removing a soil sample from the earth,*

*inserting the soil sample into a sealable vial,*

*sealing the vial with a cap, the sealed vial having a self-sealing penetrable part,*

*thereafter injecting a capturing agent through the self-sealing penetrable part into the vial without otherwise disturbing the sealed condition of the vial, and*

*thereafter analyzing the contents of the vial.*

*34. The method of claim 33 wherein the capturing agent is methanol.*

*35. The method of claim 33 further including storing the sealed vial containing the soil sample and the capturing agent before the analyzing step.*

*36. The method of claim 33 wherein the self-sealing penetrable part is positioned on the cap.*

*37. The method of claim 33 further including the step of shaking the vial after the capturing agent has been injected.*

*38. The device of claim 13 wherein the abutment surface prevents movement of the tail away from the flange when the tail abuts the abutment surface.*

* * * * *